US006770471B2

United States Patent
Barlocchi et al.

(10) Patent No.: US 6,770,471 B2
(45) Date of Patent: Aug. 3, 2004

(54) INTEGRATED CHEMICAL MICROREACTOR, THERMALLY INSULATED FROM DETECTION ELECTRODES, AND MANUFACTURING AND OPERATING METHODS THEREFOR

(75) Inventors: Gabriele Barlocchi, Cornaredo (IT); Flavio Villa, Milan (IT)

(73) Assignee: STMicroelectronics S.r.l., Agrate Brianza (IT)

(*) Notice: Subject to any disclaimer, the term of this patent is extended or adjusted under 35 U.S.C. 154(b) by 289 days.

(21) Appl. No.: 09/965,128

(22) Filed: Sep. 26, 2001

(65) Prior Publication Data

US 2002/0045244 A1 Apr. 18, 2002

(30) Foreign Application Priority Data

Sep. 27, 2000 (EP) ........................................... 00830640

(51) Int. Cl.[7] ............................................... C12M 1/34

(52) U.S. Cl. ............................... 435/287.2; 435/289.1; 435/288.5; 422/68.1; 422/102

(58) Field of Search .......................... 435/287.1, 288.5, 435/293.1, 305.1, 287.2; 422/68.1, 102

(56) References Cited

U.S. PATENT DOCUMENTS

| | | | |
|---|---|---|---|
| 5,639,423 A | 6/1997 | Northrup et al. | 122/50 |
| 5,716,842 A | 2/1998 | Baier et al. | 435/283.1 |

FOREIGN PATENT DOCUMENTS

| | | |
|---|---|---|
| EP | 0798561 A1 | 10/1997 |
| EP | 0895276 A1 | 2/1999 |
| WO | WO94/21372 | 9/1994 |
| WO | WO98/50773 | 11/1998 |
| WO | WO00/23190 | 4/2000 |

*Primary Examiner*—David A. Redding
(74) *Attorney, Agent, or Firm*—Jenkens & Gilchrist

(57) ABSTRACT

Integrated microreactor, formed in a monolithic body and including a semiconductor material region and an insulating layer; a buried channel extending in the semiconductor material region; a first and a second access trench extending in the semiconductor material region and in the insulating layer, and in communication with the buried channel; a first and a second reservoir formed on top of the insulating layer and in communication with the first and the second access trench; a suspended diaphragm formed by the insulating layer, laterally to the buried channel; and a detection electrode, supported by the suspended diaphragm, above the insulating layer, and inside the second reservoir.

11 Claims, 10 Drawing Sheets

INTEGRATED CHEMICAL MICROREACTOR, THERMALLY INSULATED FROM DETECTION ELECTRODES, AND MANUFACTURING AND OPERATING METHODS THEREFOR

BACKGROUND OF THE INVENTION

1. Field of the invention

The present invention relates to an integrated chemical microreactor, thermally insulated from the detection electrodes, and a manufacturing method therefor.

2. Description of the Related Art

As is known, some fluids are processed at temperatures that should be regulated in an increasingly more accurate way, in particular when chemical or biochemical reactions are involved. In addition to this requirement, there is often also the need to use very small quantities of fluid, owing to the cost of the fluid, or to low availability.

This is the case, for example, of the DNA amplification process (PCR, i.e., Polymerase Chain Reaction process), wherein accurate temperature control in the various steps (repeated pre-determined thermal cycles are carried out), the need to avoid as far as possible thermal gradients where fluids react (to obtain here a uniform temperature), and also reduction of the used fluid (which is very costly), are of crucial importance in obtaining good reaction efficiency, or even to make reaction successful.

Other examples of fluid processing with the above-described characteristics are associated for example with implementation of chemical and/or pharmacological analyses, and biological examinations, etc.

At present, various techniques allow thermal control of chemical or biochemical reagents. In particular, from the end of the '80s, miniaturized devices were developed, and thus had a reduced thermal mass, which could reduce the times necessary to complete the DNA amplification process. Recently, monolithic integrated devices of semiconductor material have been proposed, able to process small fluid quantities with a controlled reaction, and at a low cost (see, for example, U.S. patent application Ser. No. 09/779,980 filed on Feb. 8, 2001, and No. 09/874,382 filed on Jun. 4, 2001, assigned to STMicroelectronics, S.r.l.).

These devices comprise a semiconductor material body accommodating buried channels that are connected, via an input trench and an output trench, to an input reservoir and an output reservoir, respectively, to which the fluid to be processed is supplied, and from which the fluid is collected at the end of the reaction. Above the buried channels, heating elements and thermal sensors are provided to control the thermal conditions of the reaction (which generally requires different temperature cycles, with accurate control of the latter), and, in the output reservoir, detection electrodes are provided for examining the reacted fluid.

In chemical microreactors of the described type, the problem exists of thermally insulating the reaction area (where the buried channels and the heating elements are present) from the detection area (where the detection electrodes are present). In fact, the chemical reaction takes place at high temperature (each thermal cycle involves a temperature of up to 94° C.), whereas the detection electrodes must be kept at a constant ambient temperature.

SUMMARY OF THE INVENTION

An embodiment of the invention provides an integrated microreactor which can solve the above-described problem.

According to embodiments of the present invention, an integrated microreactor, a manufacturing method therefore and a method of operation are provided.

The integrated microreactor is formed in a monolithic body and includes a semiconductor material region and an insulating layer. A buried channel extends a distance from the surface of the semiconductor material region. First and second access trenches extend in the semiconductor material region and in the insulating layer, and in communication with the buried channel. First and second reservoirs are formed on top of the insulating layer and in communication with the first and second access trenches. A suspended diaphragm is formed in the insulating layer, laterally to the buried channel, and a detection electrode is formed, supported by the suspended diaphragm, above the insulating layer, and inside the second reservoir.

The method of operation includes introducing a reactive fluid into the buried channel, heating and cooling the fluid in the channel, extracting the fluid from the buried channel into the second reservoir and employing the detection electrode to analyze the fluid.

BRIEF DESCRIPTION OF THE DRAWINGS

In order to assist understanding of the present invention, preferred embodiments are now described, purely by way of non-limiting example, with reference to the attached drawings, wherein.

DETAILED DESCRIPTION OF THE INVENTION

Figure 1:
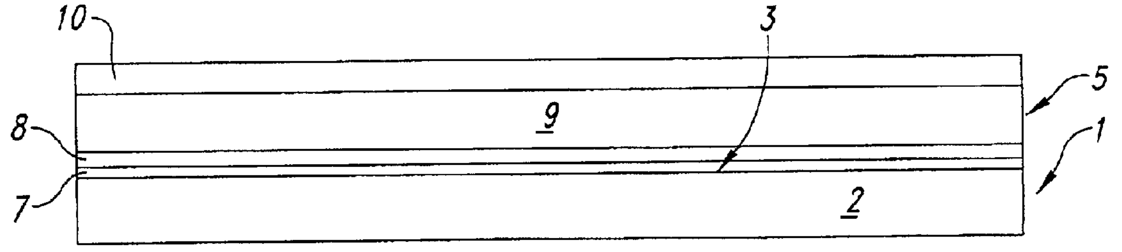
FIG. 1 shows a cross-section of a semiconductor material wafer, in an initial manufacture step of a microreactor according to the invention.
Figure 2:
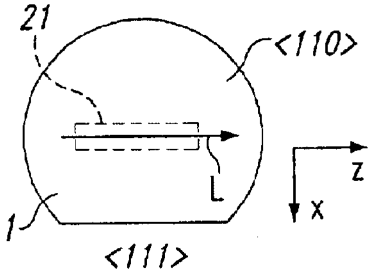
FIG. 2 shows a plan view of the wafer of FIG. 1.

As shown in FIG. 1, a wafer 1 comprises a substrate 2 of monocrystalline semiconductor material, for example silicon, having an upper surface 3. The substrate 2 has a <110> crystallographic orientation instead of <100>, as can be seen in FIG. 2, which also shows the flat of the wafer 1 with <111> orientation. FIG. 2 also shows the longitudinal direction L of a channel 21, which is still to be formed at this step.

An upper stack of layers 5 is formed on the upper surface 3 and comprises a pad oxide layer 7, of, for example, approximately 60 nm; a first nitride layer 8, of, for example, approximately 90 nm; a polysilicon layer 9, of, for example 450–900 nm; and a second nitride layer 10, of, for example, 140 nm.

Figure 4:
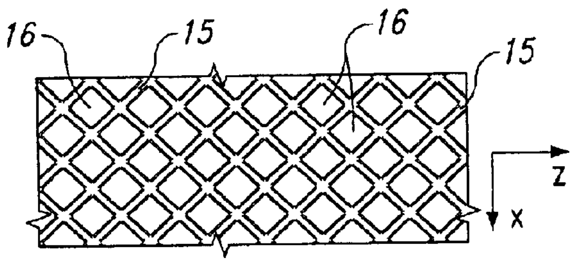
FIG. 4 shows a plan view of a portion of mask used for forming the structure of FIG. 3.

The upper stack of layers 5 is masked using a resist mask 15, which has a plurality of windows 16, arranged according to a suitable pattern, as shown in FIG. 4.

In detail, the apertures 16 have a square shape, with sides inclined at 45° with respect to a longitudinal direction of the resist mask 15, parallel to z-axis. For example, the sides of the apertures 16 are approximately 2 μm, and extend at a distance of 1.4 μm from a facing side of an adjacent aperture 16.

To allow deep channels to be formed in the substrate 2, as explained in greater detail hereinafter, the longitudinal direction z of the resist mask 15, parallel to the longitudinal direction of the buried channels to be formed in the substrate 2, is parallel to the flat of the wafer 1, which has an <111> orientation, as shown in FIG. 2.

Figure 3:
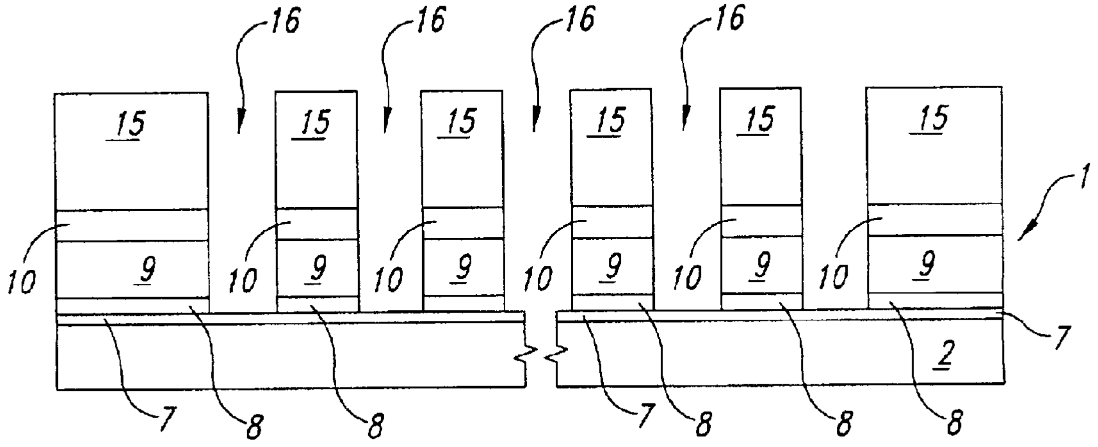
FIG. 3 shows a cross-section of the wafer of FIG. 1, in a successive manufacture step.

Using the resist mask 15, the second nitride layer 10, the polysilicon layer 9, and the first nitride layer 8 are successively etched, thus providing a hard mask 18, formed by the remaining portions of the layers 8–10, and having the same pattern as the resist mask 15 shown in FIG. 4. Thus the structure of FIG. 3 is obtained.

Figure 5:
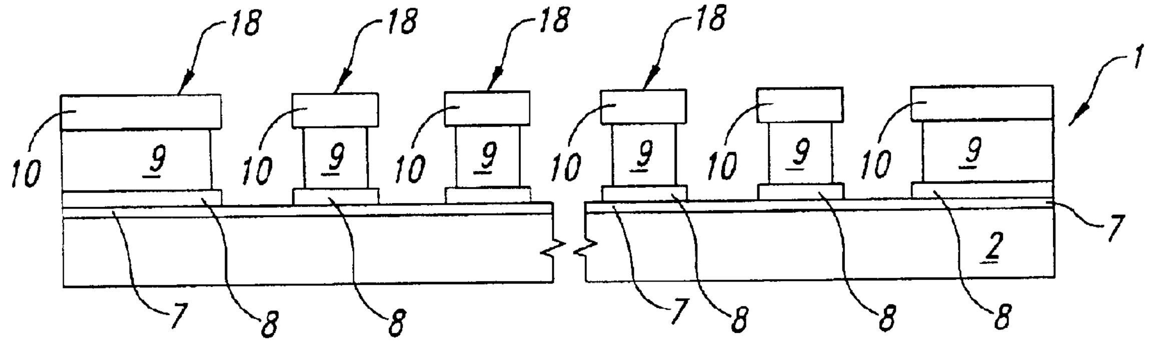
FIGS. 5–9 show cross-sections of the wafer of FIG. 3, in successive manufacturing steps.
Figure 6:
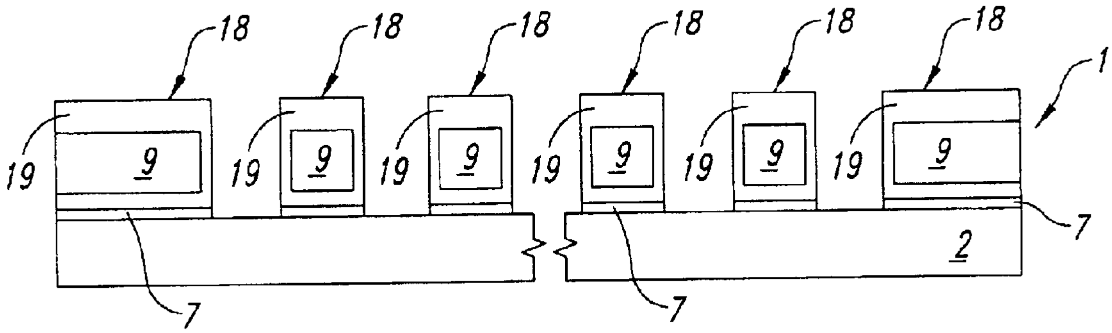

After removing the resist mask 15 (FIG. 5), the hard mask 18 is etched using TMAH (tetramethylammoniumhydroxide), such as to remove part of the uncovered polycrystalline silicon of the polysilicon layer 9 (undercut step) from the sides; a similar nitride layer is then deposited (for example with a thickness of 90 nm), which merges with the first and second nitride layers 8, 10. Subsequently, FIG. 6, the structure is dry etched, such as to completely remove the portions of conform nitride layer which extend immediately on top of the pad oxide layer 7. Thus the structure of FIG. 6 is obtained, which has a hard mask 18, grid-shaped, extending on the pad oxide layer 7, over the area where the channels are to be formed, with a form substantially reproducing the form of the resist mask 15, and is formed from the polysilicon layer 9, which is encapsulated by a covering layer 19, which in turn is formed from the nitride layers 8, 10 and from the conform nitride layer.

Figure 7:
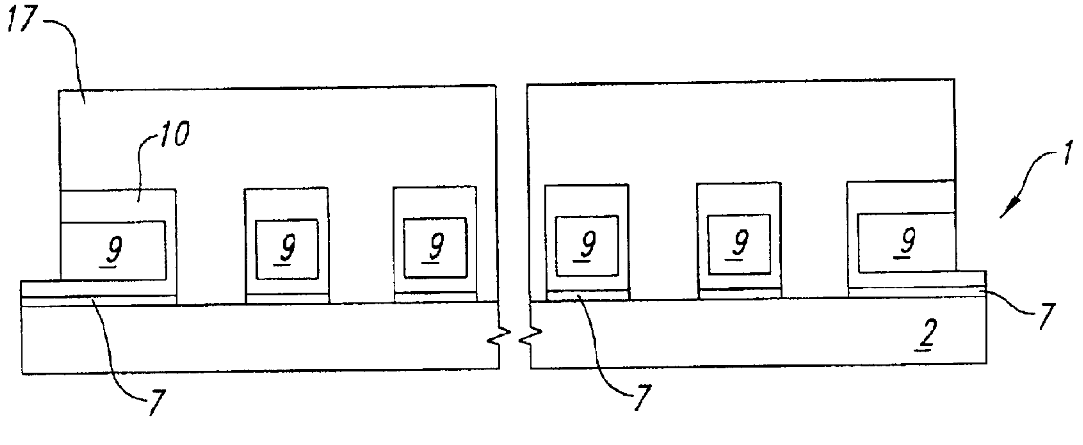
Figure 8:
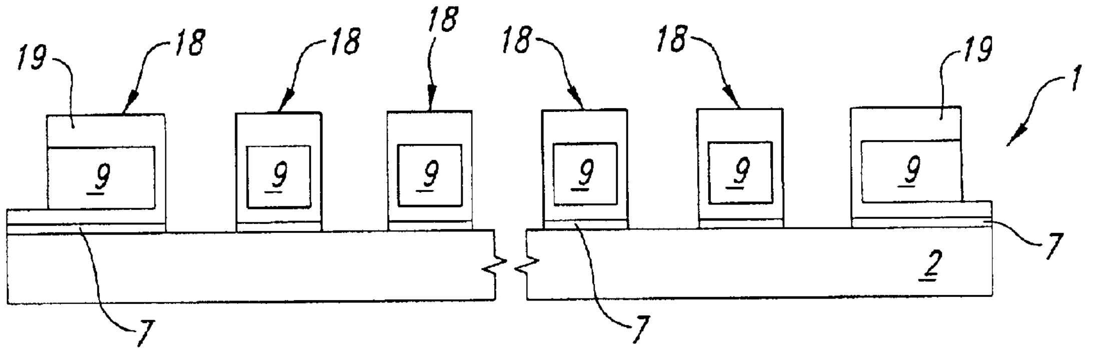

After forming the hard mask 18, FIG. 7, the second nitride layer 10 and the polysilicon layer 9 are etched externally to the area where the channels are to be formed, using a resist mask 17. After removing the resist mask 17, FIG. 8, the pad oxide layer is etched with 1:10 hydrofluoric acid, and is removed where it is exposed; in particular, externally to the area where the channels are to be formed, the pad oxide 7 is protected by the first nitride layer 8.

Figure 9:
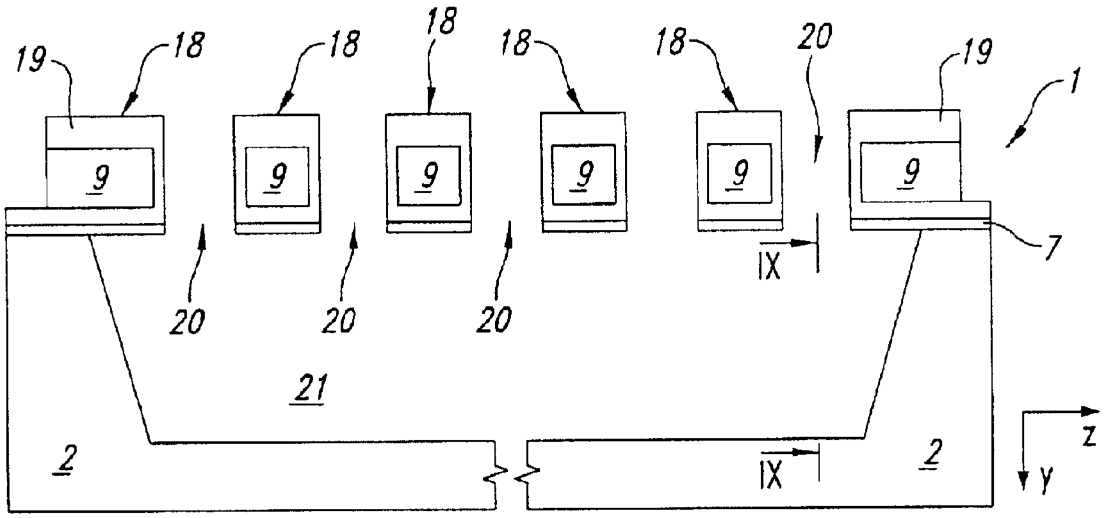

Then, FIG. 9, the monocrystalline silicon of the substrate 2 is etched using TMAH, to a depth of 500–600 μm, thus forming one or more channels 21.

Figure 10:
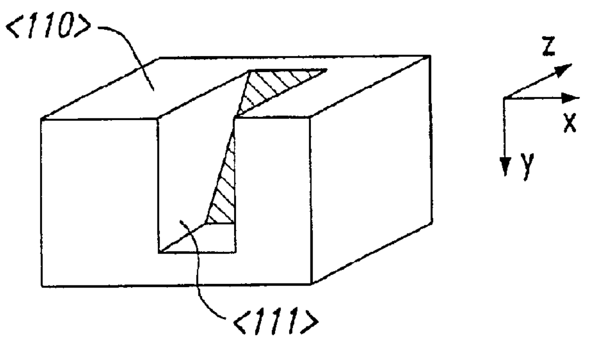
FIG. 10 shows a perspective cross-section of part of the wafer of FIG. 8.

The use of a substrate 2 with <110> orientation, the pattern of the hard mask 18, and its orientation with respect to the wafer 1, cause silicon etching to preferentially occur in y-direction (vertical), rather than in x-direction, with a speed ratio of approximately 30:1. Thereby, the TMAH etching gives rise to one or more channels 21, the vertical walls of which are parallel to the crystallographic plane <111>, as shown in the perspective cross-section of FIG. 10.

The high depth of the channels 21, which can be obtained through the described etching conditions, reduces the number of channels 21 that are necessary for processing a predetermined quantity of fluid, and thus reduces the area occupied by the channels 21. For example, if a capacity of 1 μl is desired, with a length of the channels 21 in the z-direction of 10 mm, where previously it had been proposed to form twenty channels with a width of 200 μm (in x-direction) and a depth of 25 μm (in y-direction), with a total transverse dimension of approximately 5 mm in x-direction (assuming that the channels are at a distance of 50 μm from one another), it is now possible to form only two channels 21 having a width of 100 μm in x-direction, and a depth of 500 μm, with an overall transverse dimension of 0.3 mm in x-direction, the channels being arranged at a distance of 100 μm from one another, or it is possible to form a single channel 21 with a width of 200 μm.

Figure 11:
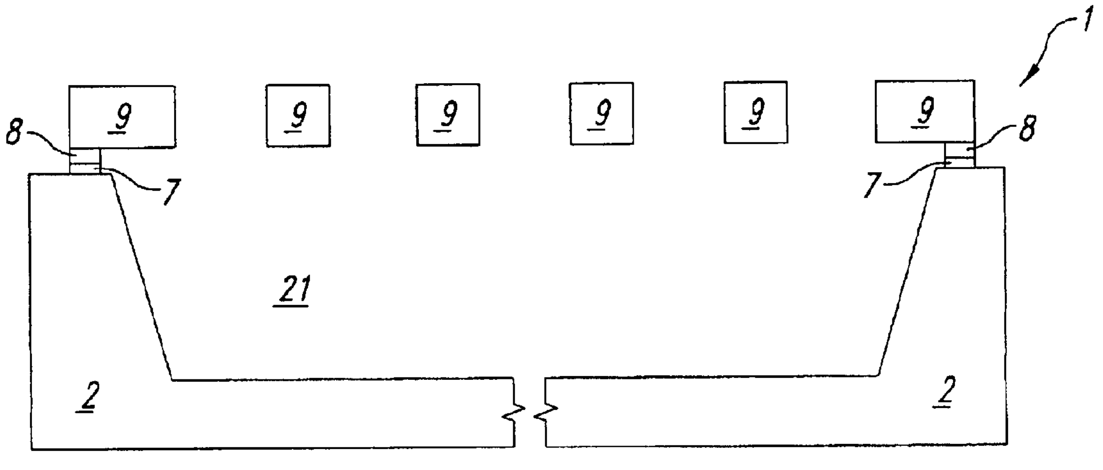
FIGS. 11–16 show cross-sections of the wafer of FIG. 9, on a reduced scale and in successive manufacture steps.

Subsequently, FIG. 11, the covering layer 19 is removed from the front of the wafer 1 (nitride layers 8, 10, conform layer, and pad oxide layer 7); in this step, the nitride and the pad oxide layers 8, 7 are also removed externally to the area of the channels 21, except on the outer periphery of the channels 21, below the polysilicon layer 9, where they form a frame region indicated at 22 as a whole.

Figure 12:
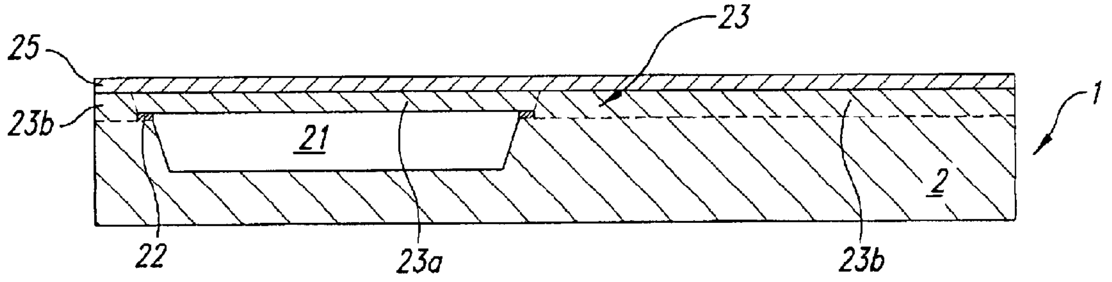

Then, FIG. 12, an epitaxial layer 23 is grown, with a thickness, for example, of 10 μm. As is known, the epitaxial growth takes place both vertically and horizontally; thus a polycrystalline epitaxial portion 23*a* grows on the polysilicon layer 9, and a monocrystalline epitaxial portion 23*b* grows on the substrate 2. A first insulating layer 25 is formed on the epitaxial layer 23; preferably, the first insulating layer 25 is obtained by thermal oxidation of silicon of the epitaxial layer 23, to a thickness of, for example, 500 nm.

Subsequently, FIG. 13, heaters 26, contact regions 27 (and related metal lines), and detection electrodes 28 are formed. To this end, a polycrystalline silicon layer is initially deposited and defined, such as to form the heating element 26; a second insulating layer 30 is provided, of deposited silicon oxide; apertures are formed in the second insulating layer 30; an aluminum-silicon layer is deposited and defined, to form the contact regions 27, interconnection lines (not shown) and a connection region 31 for the detection electrode 28; a third insulating layer 32 is deposited, for example of TEOS, and removed where the detection electrode 28 is to be provided; then titanium, nickel and gold regions are formed to make up the detection electrode 28, in a known manner.

Figure 13:
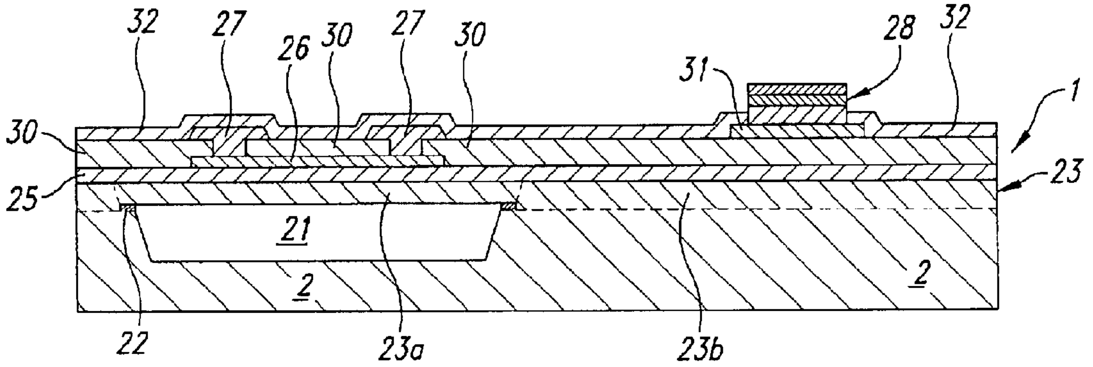

In practice, as can be seen in FIG. 13, the heating element 26 extends on top of the area occupied by the channels 21, except over the longitudinal ends of the channels 21, where input and output apertures must be provided (as described hereinafter); the contact regions are in electrical contact with two opposite ends of the heating element 26, to permit passage of electric current and heating of the area beneath, and the detection electrode 28 is laterally offset with respect to the channels 21, and extends over the epitaxial monocrystalline portion 23*b*.

Figure 14:
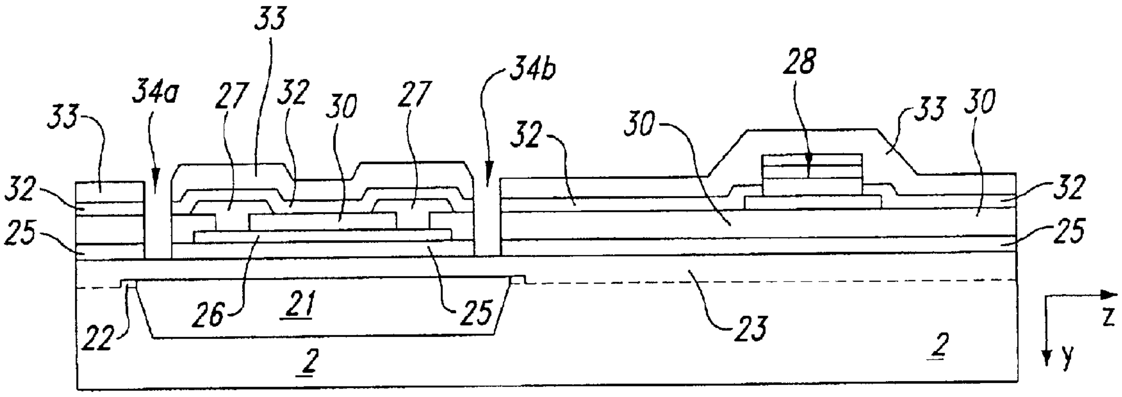

Subsequently, FIG. 14, a protective layer 33 is formed and defined on the third insulating layer 32. To this end, a standard positive resist layer can be deposited, for example of the type comprising three components, formed by a NOVOLAC resin, a photosensitive material or PAC (Photo-Active Compound), and a solvent, such as ethylmethylketone and lactic acid, which is normally used in microelectronics for defining integrated structures. As an alternative, another compatible material may be used, that allows shaping and is resistant to dry etching both of the silicon of the substrate 2, and of the material which is still to be deposited on the protective layer 33, such as a TEOS oxide.

Using the protective layer 33 as a mask, the third, the second and the first insulating layers 32, 30 and 25 are etched. Thereby, an intake aperture 34*a* and an output aperture 34*b* are obtained, and extend as far as the epitaxial layer 23, substantially aligned with the longitudinal ends of the channels 21. According to a preferred embodiment of the invention, the input aperture 34*a* and the output aperture 34*b* preferably have a same length as the overall transverse dimension of the channels 21 (in the x-direction, perpendicular to the drawing plane), and a width of approximately 60 μm, in z-direction.

Figure 15:
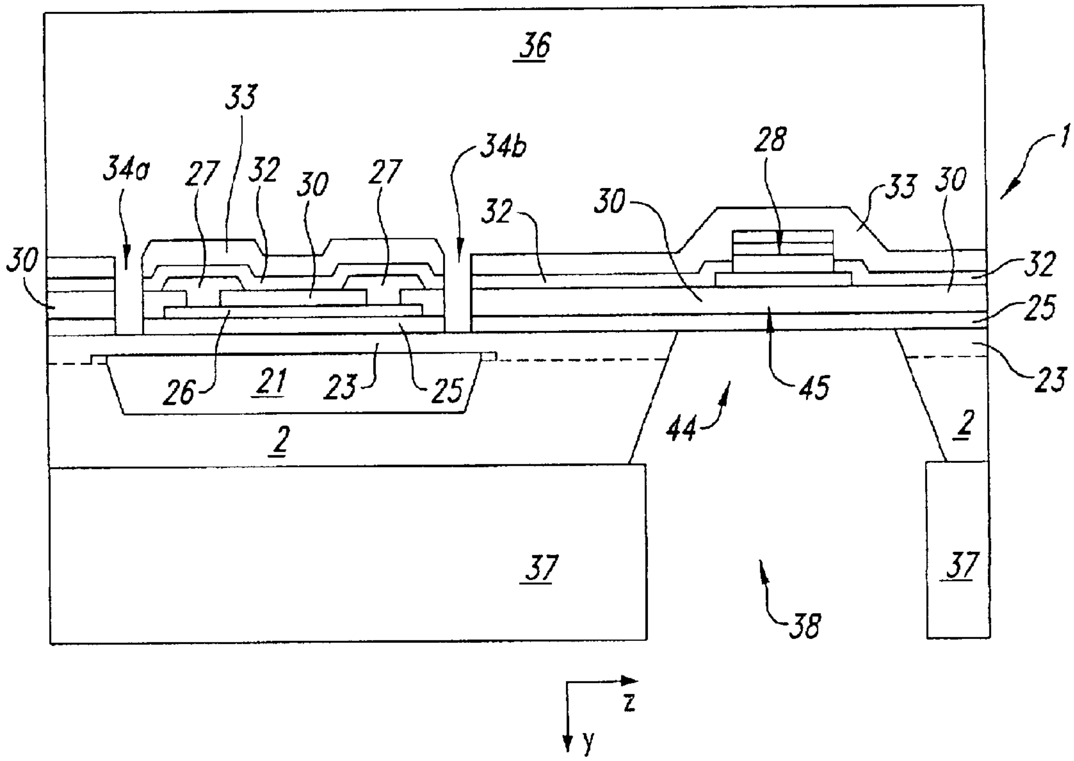

Then, FIG. 15, a negative resist layer 36 (for example THB manufactured by JSR, with a thickness of 10–20 μm) is deposited on the protective layer 33, and a back resist layer 37 is deposited and thermally treated on the rear surface of the wafer 1. The back resist layer 37 is preferably SU8 (Shell Upon 8), formed by SOTEC MICROSYSTEMS, i.e., a negative resist which has conductivity of 0.1–1.4 W/m°K, and a thermal expansion coefficient CTE ≦50 ppm/°K. For example, the back resist layer 37 has a thickness comprised between 300 μm and 1 mm, preferably of 500 μm.

Then, the back resist layer 37 is defined such as to form an aperture 38, where the monocrystalline silicon of the substrate 2 must be defined to form a suspended diaphragm.

Subsequently, the substrate 2 is etched from the back using TMAH. The TMAH etching is interrupted automatically on the first insulating layer 25, which thus acts as a stop layer. Thereby, a cavity 44 is formed on the back of the wafer 1, beneath the detection electrode 28, whereas the front side of the wafer is protected by the negative resist layer 36, which is not yet defined. The insulating layers 32, 30, 25 at the cavity 44 thus define a suspended diaphragm 45, which is exposed on both sides to the external environment, and is supported only at its perimeter.

Figure 16:
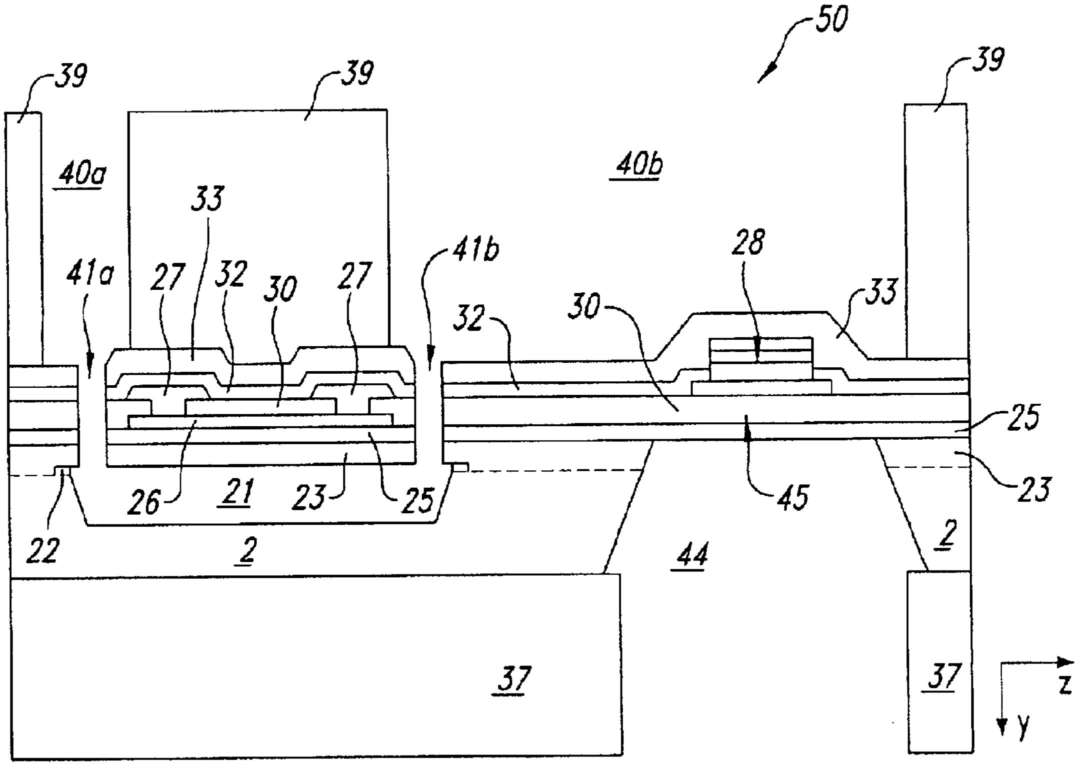

Subsequently, FIG. 16, the negative resist layer 36 is removed; then, a front resist layer 39 is deposited and thermally treated. Preferably, the front resist layer is SU8, with the same characteristics as those previously described for the back resist layer 37. Then, the front resist layer 39 is defined and forms an input reservoir 40a and an output reservoir 40b. In particular, the input reservoir 40a communicates with the input aperture 34a, whereas the output aperture 40b communicates with the output aperture 34b, and surrounds the detection electrode 28. Preferably, the reservoirs 40a, 40b have a length (in x-direction, perpendicular to the plane of FIG. 16) which is slightly longer than the overall transverse dimension of the channels 21; the input reservoir 40a has a width (in z-direction) comprised between 300 μm and 1.5 mm, preferably approximately 1 mm, and has a thickness (in y direction) preferably comprised between 300 μm and 400 μm, so as to yield a volume of at least 1 $mm^3$. The output reservoir 40b has a width (in z-direction) comprised between 1 and 4 mm, preferably of approximately 2.5 mm.

Then, FIG. 16, using as a masking layer the front resist layer 39 and the protective layer 33, the substrate 2 is trench-etched, so as to remove silicon from below the input and output apertures 34a, 34b (FIG. 15). Thus access trenches 41a, 41b are formed, incorporate the intake and output apertures 34a, 34b, and extend as far as the channels 21, such as to connect the channels 21 in parallel, to the input reservoir 40a and to the output reservoir 40b.

Finally, the exposed portion of the protective layer 33 is removed, such as to expose the detection electrode 28 once more, and the wafer 1 is cut into dice, to give a plurality of microreactors formed in a monolithic body 50.

The advantages of the described microreactor are as follows. First, forming detection electrodes 28 on suspended diaphragms 45 that are exposed on both sides, ensures that the electrodes are kept at ambient temperature, irrespective of the temperature at which the channels 21 are maintained during the reaction.

The thermal insulation between the detection electrodes 28 and the channels 21 is also increased by the presence of insulating material (insulating layers 25, 30 and 32) between the detection electrodes 28 and the epitaxial layer 23, which, while functioning primarily as electrical insulation, also contributes to the thermal isolation of the detection electrodes 28.

The microreactor has greatly reduced dimensions, owing to the high depth of the channels 21, which, as previously stated, reduces the number of channels necessary per unit of volume of processed fluid. In addition, the manufacture requires steps that are conventional in microelectronics, with reduced costs per item; the process also has low criticality and a high productivity, and does not require the use of critical materials.

Finally, it is apparent that many modifications and variants can be made to the microreactor and manufacturing method as described and illustrated here, all of which come within the scope of the invention, as defined in the attached claims.

For example, the material of the diaphragm 45 can differ from that described; for example the first and the second insulating layers 25, 30 can consist of silicon nitride, instead of, or besides, oxide.

The resist type used for forming the layers 33, 36, 37 and 39 can be different from those described; for example, the protective layer 33 can consist of a negative resist, instead of a positive resist, or of another protective material that is resistant to etching both of the front and back resist layers 39, 37 and of the silicon, and can be removed selectively with respect to the second insulating layer 30; and the front and back resist layers 39, 37 can consist of a positive resist, instead of in a negative resist. In addition, according to a variant described in the aforementioned European patent application 00830400.8, the input and output reservoirs can be formed in photosensitive dry resist layer. In this case, the access trenches can be formed before applying the photosensitive dry resist layer.

According to a different embodiment, the negative resist layer 36 is not used, and the front resist layer 39 is directly deposited; then, before defining the back resist layer 37 and etching the substrate 2 from the back, the front resist layer 39 is defined to form the reservoirs 40a, 40b, and then the access trenches 41a, 41b; in this case, subsequently, by protecting the front of the wafer with a support structure having sealing rings, the cavity 44 is formed and the diaphragm 45 is defined.

Figure 18:
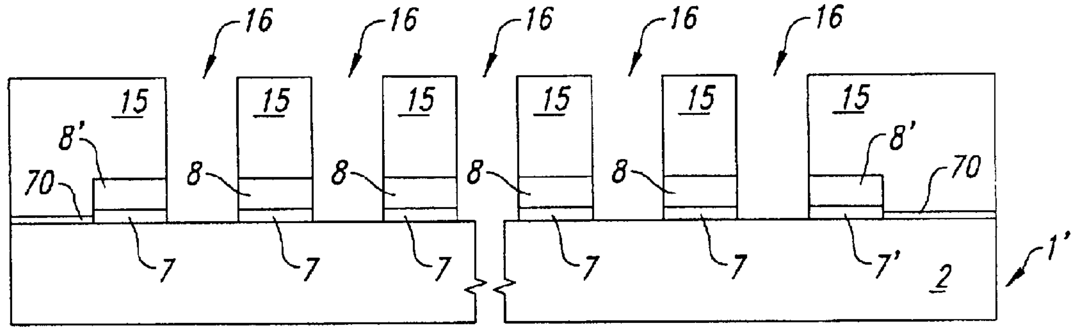
Figure 19:
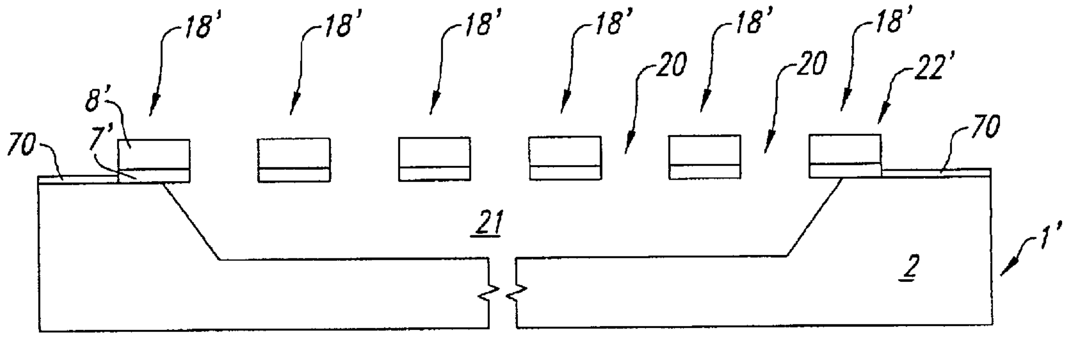
Figure 20:
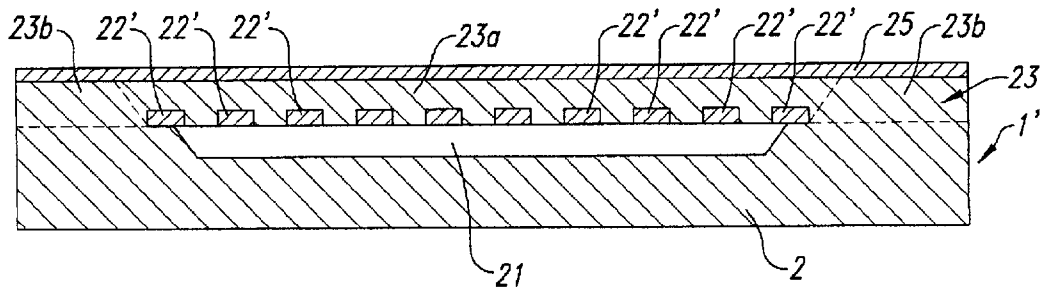

Finally, if the channels 21 must have a reduced thickness (25 μm, up to 100 μm), the hard mask 18' can be formed simply from a pad oxide layer and from a nitride layer. In this case, FIG. 17, the pad oxide layer and the nitride layer are formed on the substrate 2 of a wafer 1'. Then, the pad oxide layer and the nitride layer are removed externally from the area of the channels, thus forming a pad oxide region 7' and a nitride region 8'; subsequently, a second pad oxide layer 70 is grown on the substrate 2. Then, FIG. 18, the wafer 1' is masked with the resist mask 15 which has windows 16, similarly to FIG. 3; subsequently, FIG. 19, TMAH etching is carried out to form channels 21, using the hard mask 18'. In this step, the substrate 2 is protected externally to the channel area by the second pad oxide layer 70. Then, FIG. 20, the second pad oxide layer 70, and partially also the first pad oxide layer 7', which must have appropriate dimensions, are removed with HF externally to the channel area, leaving intact the remaining portions 22' of the pad oxide layer 7' and the nitride layer 8', and epitaxial growth is carried out using silane at a low temperature.

In these conditions, germination of silicon takes place also on nitride; in particular, an epitaxial layer 23, which has a polycrystalline portion 23*a*, on the hard mask 18', and a monocrystalline portion 23*b*, on the substrate 2 is grown, similarly to FIG. 12. The remaining operations then follow, until a monolithic body 50 is obtained (FIG. 16), as previously described.

Figure 17:
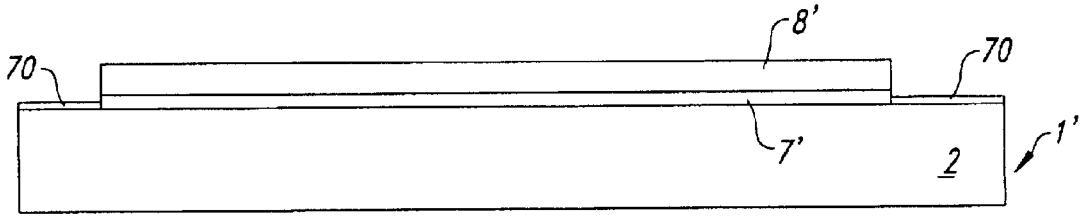
FIGS. 17–20 show cross-sections of a semiconductor material wafer, in successive manufacture steps according to a different embodiment of the invention.

As an alternative to the arrangement shown in FIG. 17, the pad oxide layer 7' and the nitride layer 8' are not removed externally of the channel area; and, after the channels 21 have been formed (FIG. 19), oxide is grown and covers the walls of the channels 21, a TEOS layer is deposited and closes the portions 22' at the top; the dielectric layers are removed externally of the channel area using a suitable mask, down to the substrate 2; and finally the epitaxial layer 23 is grown.

The present method can also be applied to standard substrates with <100> orientation, if high depths of the channels are not necessary.

The method of operation of the device is as follows, according to one embodiment of the invention. The channels 21 function as a reactor cavity. A reactive fluid is introduced into the input reservoir 40*a* and thence into the channels 21 via the access trench 41*a*. This may be accomplished by capillary action or by appropriate air pressure, or other acceptable techniques. In the case of a PCR operation, the fluid is heated and cooled repeatedly according to specific parameters, which parameters may be custom for each particular applications and fluid type. The setting of such parameters is within the skill of those in the art. The heating is accomplished by the use of the heating element 32 using known methods. The cooling step may be carried out by removing the heat and permitting the fluid to cool towards the ambient. Cooling may be accelerated by the use of a heat sink attached in a known manner to the semiconductor body 2. Other cooling means may be employed as appropriate, for example, a cooling fan, by the circulation of a liquid coolant, or by the use of a thermocouple.

Throughout the heating and cooling process the detection electrode 28 remains at ambient temperature, owing to the thermal insulation afforded by the presence of the diaphragm 45 and the insulation layers 25, 30, and 32, as required for proper operation of the detection electrode.

At the conclusion of the heating and cooling cycles the fluid is removed from the channels 21 via the access trench 41*b*, into the output reservoir 40*b*, by the application of air pressure, or by other means as appropriate. The detection electrode 28 is employed to detect a desired product of the reaction process in the fluid. This detection process is within the skill of those practiced in the art, and so will not be described in detail.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An integrated microreactor, comprising: a monolithic body, having a semiconductor material region; a buried channel, extending inside said semiconductor material region; a first and a second access cavity, extending in said monolithic body, and in communication with said buried channel; a suspended diaphragm formed from said monolithic body, laterally to said buried channel; and a detection electrode, supported by said suspended diaphragm, wherein said monolithic body comprises an insulating region, superimposed to said semiconductor material region, and forming said suspended diaphragm, and wherein said monolithic body comprises a reservoir region, extending on top of said insulating region, and defines a first and a second reservoir, connected respectively to a first and a second trench, said first and a second trench extending through said insulating region and said semiconductor material region, as far as said buried channel, said second reservoir accommodating said detection electrode.

2. A microreactor according to claim 1, having a heating element, extending over said semiconductor material region, on top of said buried channel.

3. A microreactor according to claim 2, wherein said heating element is embedded in said insulating region.

4. A microreactor according to claim 1, wherein said detection electrode extends on top of said insulating region.

5. A microreactor according to claim 1, wherein said semiconductor material region comprises a monocrystalline substrate and an epitaxial layer, superimposed on one another.

6. A microreactor according to claim 5, wherein said semiconductor material region has a cavity extending beneath said diaphragm, as far as said insulating region.

7. A microreactor according to claim 1, wherein said buried channel has a depth of up to 600–700 $\mu$m.

8. An integrated microreactor, comprising: a monolithic body, having a semiconductor material region; a buried channel, extending inside said semiconductor material region; a first and a second access cavity, extending in said monolithic body, and in communication with said buried channel; a suspended diaphragm formed from said monolithic body, laterally to said buried channel; and a detection electrode, supported by said suspended diaphragm, wherein said semiconductor material region comprises a monocrystalline substrate, with a <110> crystallographic orientation, and wherein said buried channel has a longitudinal direction that is substantially parallel to a crystallographic plane with a <111> orientation.

9. A structure comprising: a semiconductor material body; a buried channel formed in the semiconductor material body at a distance from a surface of the semiconductor material body; first and second trenches, formed on the semiconductor material body, extending from a top surface of the semiconductor material body to first and second ends, respectively, of the buried channel; a heating element, formed on the semiconductor material body above the buried channel; a suspended diaphragm, formed on the semiconductor material body and adjacent to the buried channel; and a sensing electrode structure, formed on the semiconductor material body above the suspended diaphragm.

10. The structure of claim 9, further comprising first and second reservoirs, formed on the surface of the semiconductor material body, wherein the first reservoir is above the first trench such that the first trench connects the first reservoir with the first end of the buried channel, and the second reservoir is above the second trench such that the second trench connects the second reservoir with the second end of the buried channel, and such that the second reservoir extends onto the suspended diaphragm, with the sensing electrode structure inside the second reservoir.

11. The structure of claim 10 wherein the first and second reservoirs are formed in, and defined by a resist layer formed on the surface of the semiconductor material body.

* * * * *